(12) United States Patent
Copland

(10) Patent No.: US 8,730,463 B2
(45) Date of Patent: May 20, 2014

(54) METHOD OF VERIFYING PERFORMANCE OF AN OPTICAL MEASUREMENT INSTRUMENT WITH A MODEL EYE AND AN OPTICAL MEASUREMENT INSTRUMENT EMPLOYING SUCH A METHOD

(75) Inventor: James Copland, Albuquerque, NM (US)

(73) Assignee: AMO Wavefront Sciences, LLC., Santa Ana, CA (US)

( * ) Notice: Subject to any disclaimer, the term of this patent is extended or adjusted under 35 U.S.C. 154(b) by 36 days.

(21) Appl. No.: 13/480,800

(22) Filed: May 25, 2012

(65) Prior Publication Data
US 2012/0300196 A1 Nov. 29, 2012

Related U.S. Application Data

(60) Provisional application No. 61/490,139, filed on May 26, 2011.

(51) Int. Cl.
*G01B 11/26* (2006.01)

(52) U.S. Cl.
CPC ..................................... *G01B 11/26* (2013.01)
USPC ....................................................... 356/138

(58) Field of Classification Search
CPC ..................................................... G01B 11/26
USPC ............................ 351/205–208; 356/138–155
See application file for complete search history.

(56) References Cited

U.S. PATENT DOCUMENTS

| | | |
|---|---|---|
| 1,630,944 A | 5/1927 | Ingersoll |
| 2,068,950 A | 1/1937 | Hamilton |
| 4,253,743 A | 3/1981 | Matsumura |
| 5,042,938 A | 8/1991 | Shimozono |
| 6,485,142 B1 | 11/2002 | Sheehy et al. |
| 6,588,902 B2 * | 7/2003 | Isogai ........................... 351/208 |
| 6,626,535 B2 | 9/2003 | Altmann |
| 6,802,609 B2 | 10/2004 | Mihashi et al. |
| 7,036,933 B2 | 5/2006 | Yamaguchi et al. |
| 7,425,067 B2 | 9/2008 | Warden et al. |
| 7,742,244 B2 | 6/2010 | Liu et al. |
| 7,792,249 B2 | 9/2010 | Gertner et al. |
| 2002/0041359 A1 | 4/2002 | Mihashi et al. |
| 2003/0025877 A1 | 2/2003 | Yancey et al. |

(Continued)

FOREIGN PATENT DOCUMENTS

| | | |
|---|---|---|
| DE | 102006025638 A1 | 12/2007 |
| DE | 102008055755 A1 | 5/2010 |

(Continued)

OTHER PUBLICATIONS

International Search Report and Written Opinion for Application No. PCT/US2012/039553, mailed on Aug. 23, 2012, 15 pages.

*Primary Examiner* — Michael P Stafira
(74) *Attorney, Agent, or Firm* — AMO Wavefront Sciences, LLC.

(57) ABSTRACT

A method of compensating for misalignment between an optical measurement instrument and a model eye includes: receiving a light beam from the model eye at the optical measurement instrument; producing image data, including light spot data for a plurality of light spots, from the received light beam; determining an observed location of a corneal reflex from the model eye within an image representing the image data; and determining an angle of misalignment between an axis normal to the front surface of the model eye and the optical axis of the optical measurement instrument from the observed location of the corneal reflex within the image.

20 Claims, 7 Drawing Sheets

(56) References Cited

U.S. PATENT DOCUMENTS

| | | |
|---|---|---|
| 2003/0174755 A1 | 9/2003 | Lai et al. |
| 2010/0002311 A1 | 1/2010 | Reichert |
| 2010/0123873 A1* | 5/2010 | Raymond et al. ............. 351/212 |
| 2011/0202046 A1* | 8/2011 | Angeley et al. .................. 606/6 |
| 2011/0279777 A1* | 11/2011 | Yee et al. ...................... 351/211 |
| 2012/0188505 A1 | 7/2012 | Copland |

FOREIGN PATENT DOCUMENTS

| | | |
|---|---|---|
| WO | WO03049606 A2 | 6/2003 |
| WO | WO2005047938 A2 | 5/2005 |
| WO | WO2010086304 A1 | 8/2010 |

* cited by examiner

METHOD OF VERIFYING PERFORMANCE OF AN OPTICAL MEASUREMENT INSTRUMENT WITH A MODEL EYE AND AN OPTICAL MEASUREMENT INSTRUMENT EMPLOYING SUCH A METHOD

CROSS-REFERENCES TO RELATED APPLICATION

This application claims priority to U.S. Provisional Application No. 61/490,139, filed on May 26, 2011, the entirety of which is hereby incorporated by reference.

BACKGROUND AND SUMMARY

1. Field

This invention pertains to optical measurement instruments, and in particular a method of verifying the correct operation of an optical measurement instrument by using a model eye, and an optical measurement instrument that employs such a method.

2. Description

It is sometimes necessary to be able to verify correct operation and specified performance of an optical measurement instrument such as a wavefront aberrometer in an operational setting. In many instances, this is done by operating the optical measurement instrument to make a measurement of a model eye whose characteristics are known. A common version of a model eye is a solid glass or plastic component with a curved front surface and a flat back surface. The front curve serves the role of a "cornea" for the model eye, and the back surface serves as a "retina" for the model eye. Some model eyes have a limiting aperture that serves as an "iris" for the model eye. The aperture is most commonly located in front of the front surface of the model eye, but it can also be inside the model eye.

To verify correct operation and specified performance of an optical measurement instrument, typically the optical measurement instrument injects a probe beam into a front surface of the model eye. Light scatters from the back surface of the model eye similarly to the way it does with a human eye, and some of the scattered light travels back out of the front surface of the model eye and into the optical measurement instrument. From the received light, the optical measurement instrument makes one or more measurements of the model eye. Typically, the optical measurement instrument measures the sphere and/or cylinder values of the model eye, and compares these measured values with corresponding predetermined calibration data for the model eye to determine whether or not the optical measurement instrument is operating properly. The values must agree within some tolerance for the optical measurement instrument to be considered in good working order.

However, the values for sphere and cylinder that an optical measuring instrument measures will vary depending on the angle that an axis normal to the model eye makes with respect to the optical measurement instrument's optical axis (hereinafter referred to as "the misalignment angle"). The predetermined calibration data assumes a misalignment value of zero degrees. Even when the optical measurement instrument is operating perfectly, when the misalignment angle is not zero degrees then there will be a variance between the measured sphere and cylinder values for the model eye and the predetermined calibration values. This variation in the measured sphere and/or cylinder values that depends on the misalignment angle between the optical measurement instrument and the model eye makes it hard to verify proper operation of the optical measurement instrument. For example, experiments have been performed with an example optical measurement instrument making measurements on a model eye that has a front surface curvature that matches that of a human cornea. With a misalignment angle of only three (3) degrees, the model eye measurements were 0.5 Diopters different from the calibration value for perfect alignment (i.e., zero degree misalignment angle). This variation was far in excess of the maximum tolerable variation of 0.1 Diopters for the example optical measurement instrument.

It should be noted that the problem described here is unique to measuring model eyes. This misalignment does not occur when measuring a human eye, because the patient directs their gaze straight into the optical measurement instrument to view a fixation target of the optical measurement instrument, thus automatically aligning the human eye with the optical axis of the optical measurement instrument.

In contrast to this simple method of aligning a human eye by means of a fixation target, it may be difficult and/or time-consuming for an operator through trial-and-error to achieve a degree of alignment between a model eye and the optical measurement instrument's optical axis that renders insignificant the variation in the measured sphere and/or cylinder. One solution is to constrain the model eye by mechanical means so it points directly toward the optical measurement instrument. However, this approach adds expense to the model eye mount and may not reduce the measurement variation to within a desired tolerance.

Therefore, it would be desirable to provide a method of verifying proper operation with an optical measurement instrument with a model eye that can address variations in measurements that occur when the model eye is misaligned with respect to the optical measurement instrument. It would also be desirable to provide an optical measurement instrument that can operate with such a method.

In one aspect of the invention, a method comprises: receiving a light beam from a model eye at an optical measurement instrument having an optical axis; producing image data, including light spot data for a plurality of light spots, from the received light beam; determining an observed location of a corneal reflex from the model eye within an image representing the image data; and determining an angle of misalignment between an axis normal to the front surface of the model eye and the optical axis of the optical measurement instrument from the observed location of the corneal reflex within the image.

In another aspect of the invention, a measurement instrument comprises: one or more light sources configured to illuminate a model eye; a light spot generator configured to receive light from the model eye and to generate a plurality of light spots from the light received from the illuminated object; a detector configured to detect the light spots and for outputting image data, including light spot data for the plurality of light spots; and a processor. The processor is configured to process the image data to determine an alignment between the measurement instrument and the model eye by: determining an observed location of a corneal reflex from the model eye within an image representing the light spot data; and determining an angle of misalignment between an axis normal to the front surface of the model eye and an optical axis of the measurement instrument from the observed location of the corneal reflex within the image.

In yet another aspect of the invention, a method is provided for determining a misalignment between a measurement instrument and a model eye used to verify correct operation of the measurement instrument, by determining a difference between: (1) an observed location of a corneal reflex in an image produced by the measurement instrument from the model eye, and (2) an expected location of the corneal reflex.

In still another aspect of the invention, a method comprises: receiving a light beam from a model eye at an optical measurement instrument having an optical axis; producing image data, including light spot data for a plurality of light spots, from the received light beam; determining an observed location of a corneal reflex from the model eye within an image representing the image data; defining an analysis area within an image represented by the image data, wherein the analysis area is centered on the observed location of the corneal reflex; and measuring at least one of a sphere value and a cylinder value for the model eye from a portion of the light spot data corresponding to light spots within the analysis area.

DETAILED DESCRIPTION

Exemplary embodiments of model eyes and methods for verifying proper operation and performance of optical measurement equipment through use of a model eye will be described in some detail below so as to illustrate various aspects and advantages of these devices and methods. However, it should be understood that the principles involved in these devices and methods can be employed in a variety of other contexts, and therefore the novel devices and method disclosed and claimed here should not be construed as being limited to the example embodiments described below.

Figure 1:
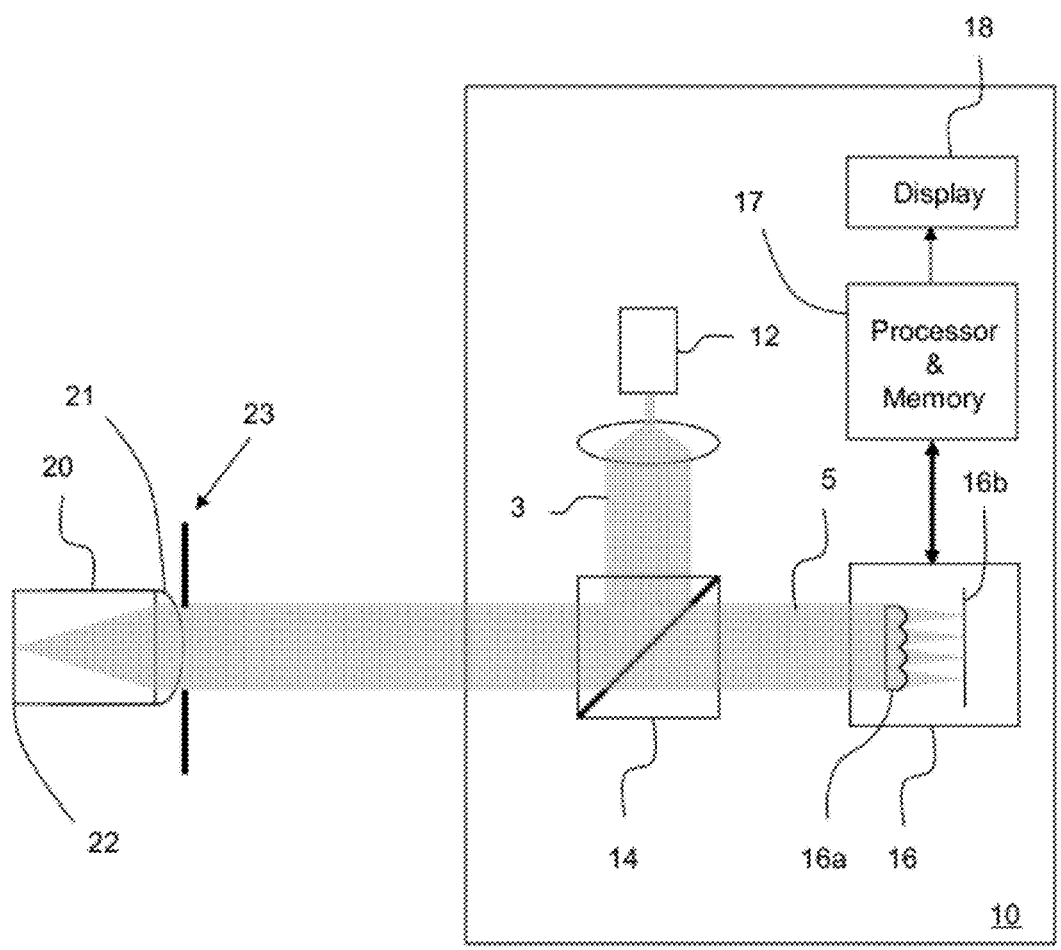
FIG. 1 illustrates an example embodiment of an optical measurement instrument making a measurement with an example embodiment of a model eye to verify correct operation and specified performance of the optical measurement instrument.

FIG. 1 illustrates an example embodiment of an optical measurement instrument 10 making a measurement with an example embodiment of a model eye 20 to verify correct operation and specified performance of an optical measurement instrument. Here optical measurement instrument 10 may be a wavefront aberrometer. Optical measurement instrument 10 includes, among other elements, a coherent light source (e.g., a laser or SLD) 12, a beamsplitter 14, a wavefront sensor 16, a processor 17 and associated memory, and optionally a display 18. In some embodiments wavefront sensor 16 may be a Shack-Hartmann wavefront sensor including a lenslet array 16a and a pixel array 16b (e.g., camera, charge-coupled-device (CCD) or CMOS array). In various embodiments, optical measurement instrument 10 may include a variety of other elements not shown in FIG. 1, such as optical elements (e.g., lenses, mirrors, etc.), a fixation target, aperture stops, etc. Processor 17 may execute algorithms to control operations of optical measurement instrument 10, for example by executing instructions in accordance with program code stored in the associated memory, which may include one or more of volatile memory (e.g., random access memory), nonvolatile memory, Flash memory, a hard disk drive, optical disk drive, etc. Processor 17 may operate according to n operating system, which may be a generic operating system such as WINDOWS®, MACINTOSH® Operating System, UNIX, etc., or may employ a custom operating system. Processor 17 may provide a user interface (e.g., a graphical user interface) for an operator of optical measurement instrument 10 and may display measurement results via display 18.

Model eye 20 has a front surface 21, and a rear or back surface 22, and an iris 23. Front surface 21 may be curved to focus light onto rear surface 22 such that front surface 21 acts as a "cornea" for model eye 20, and rear surface 22 acts as a "retina" for model eye 20.

Figure 2:
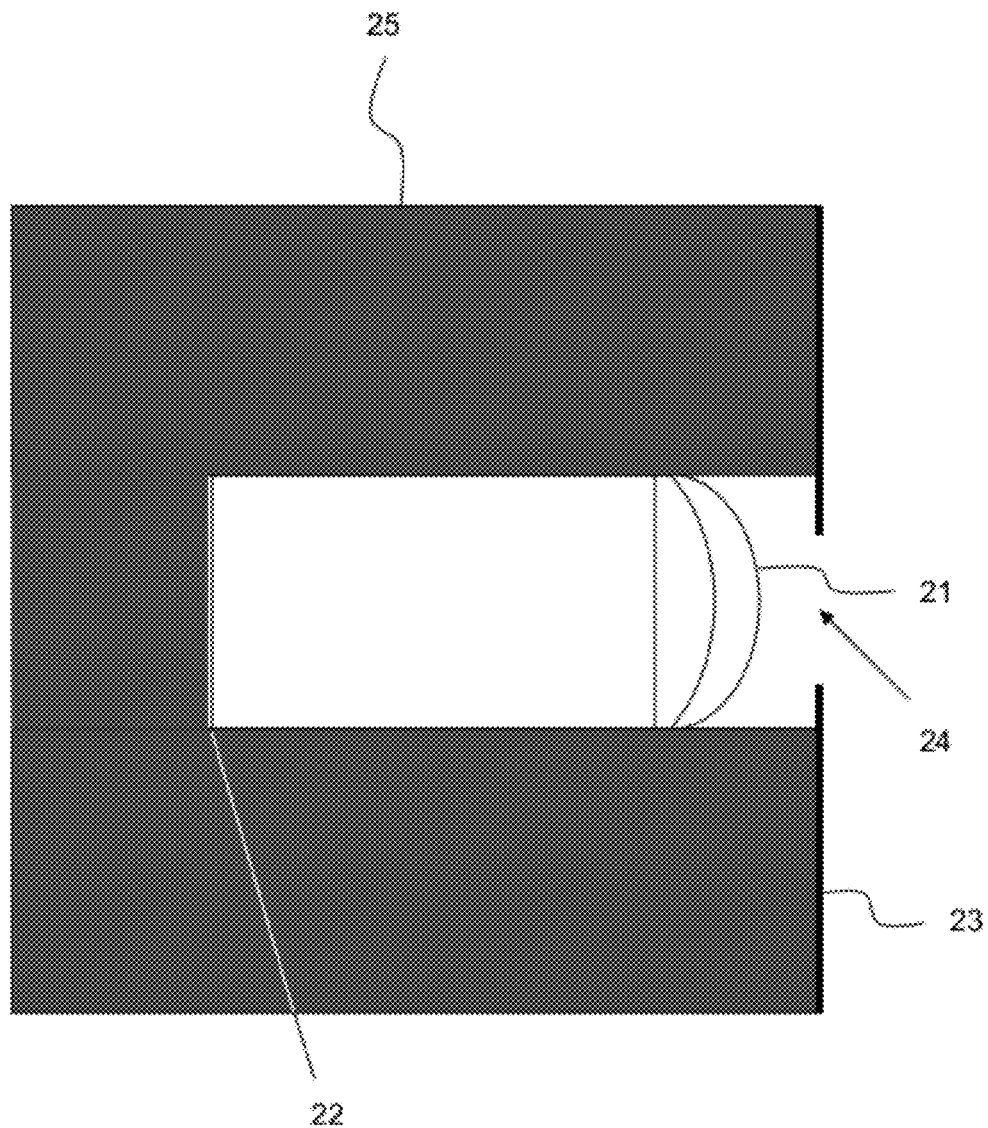
FIG. 2 illustrates one example embodiment of a model eye.

FIG. 2 illustrates in greater detail one example embodiment of model eye 20. Model eye 20 includes a model eye holder or mount 25, and an opaque structure 22 having an aperture 24 therethrough disposed in front of the front surface 21 and which may act as an "iris" for model eye 20. Beneficially, mount 35 may be adjustable by an operator in x, y, z directions, and may be tiltable and rotatable.

To verify that optical measurement instrument 10 is performing correctly, coherent light source 12 generates a probe light beam 3 which is injected into front surface 21 of model eye 20. Light scatters from rear surface 22 of model eye 20 and some of the scattered light travels back out of front surface 21 and into optical measurement instrument 10 as a return beam 5. Return light beam 5 is provided to wavefront sensor 16 which can operate with processor 17 to make one or more measurements of one or more characteristics of model eye 20, for example a sphere and/or cylinder value for model eye 20. The measured value(s) can be compared with known or previously measured calibration value(s) of sphere and/or cylinder of model eye 20 to allow a determination to be made as to whether optical measurement instrument 10 is operating correctly and/or within its specified performance tolerances.

As noted above, in practice it can be difficult to precisely align optical measurement instrument 10 and model eye 20.

Figure 3:
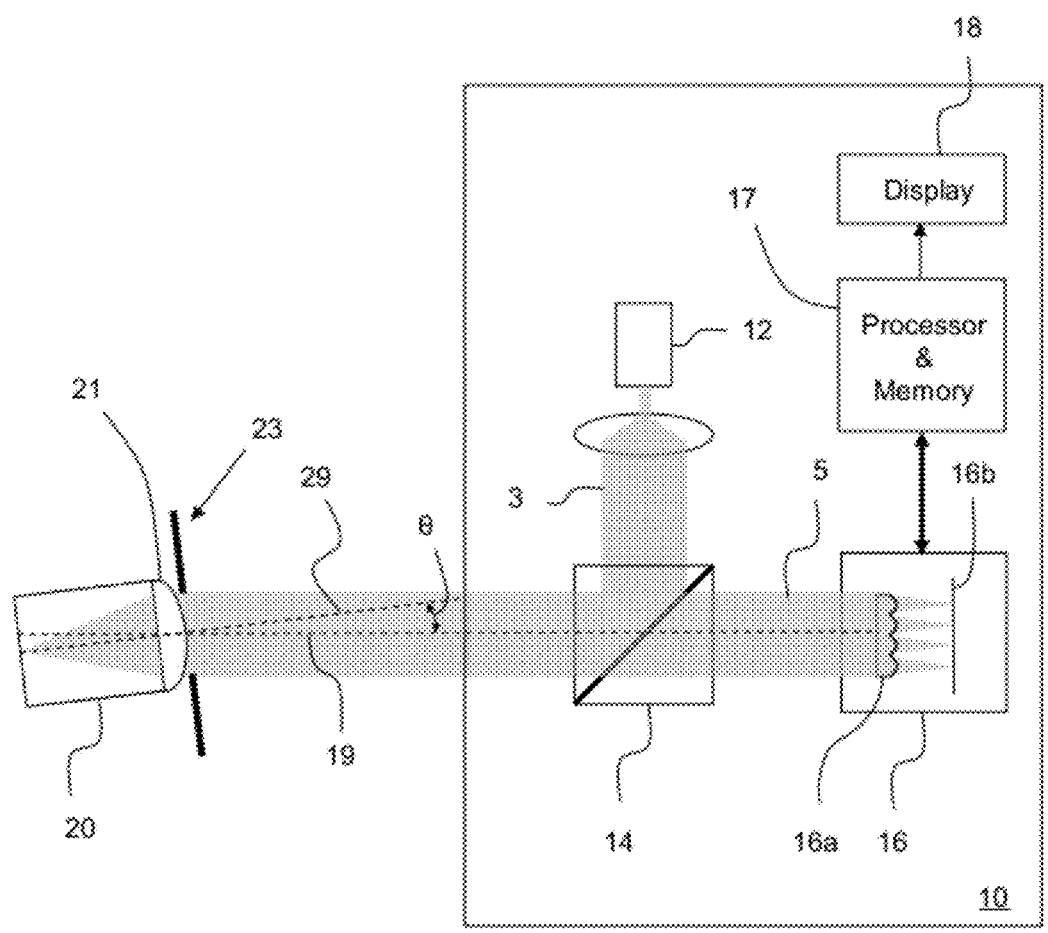
FIG. 3 illustrates an example of a misalignment between an optical measurement instrument and a model eye used to verify correct operation and specified performance of the optical measurement instrument.

FIG. 3 illustrates an example of a misalignment between optical measurement instrument 10 and model eye 20. As shown in FIG. 2, optical measurement instrument 10 has an optical axis 19 corresponding to the axis upon which probe light beam 3 is directed toward model eye 20. FIG. 3 also illustrates an axis 29 normal to the front surface 21 or "cornea" of model eye. FIG. 3 also illustrates a misalignment angle θ between optical axis 19 and normal axis 29. For clarity of illustration, misalignment angle θ is somewhat exaggerated in FIG. 3 compared to a typical example where misalignment angle θ might be more in the range of about three degrees or so.

Figure 4:
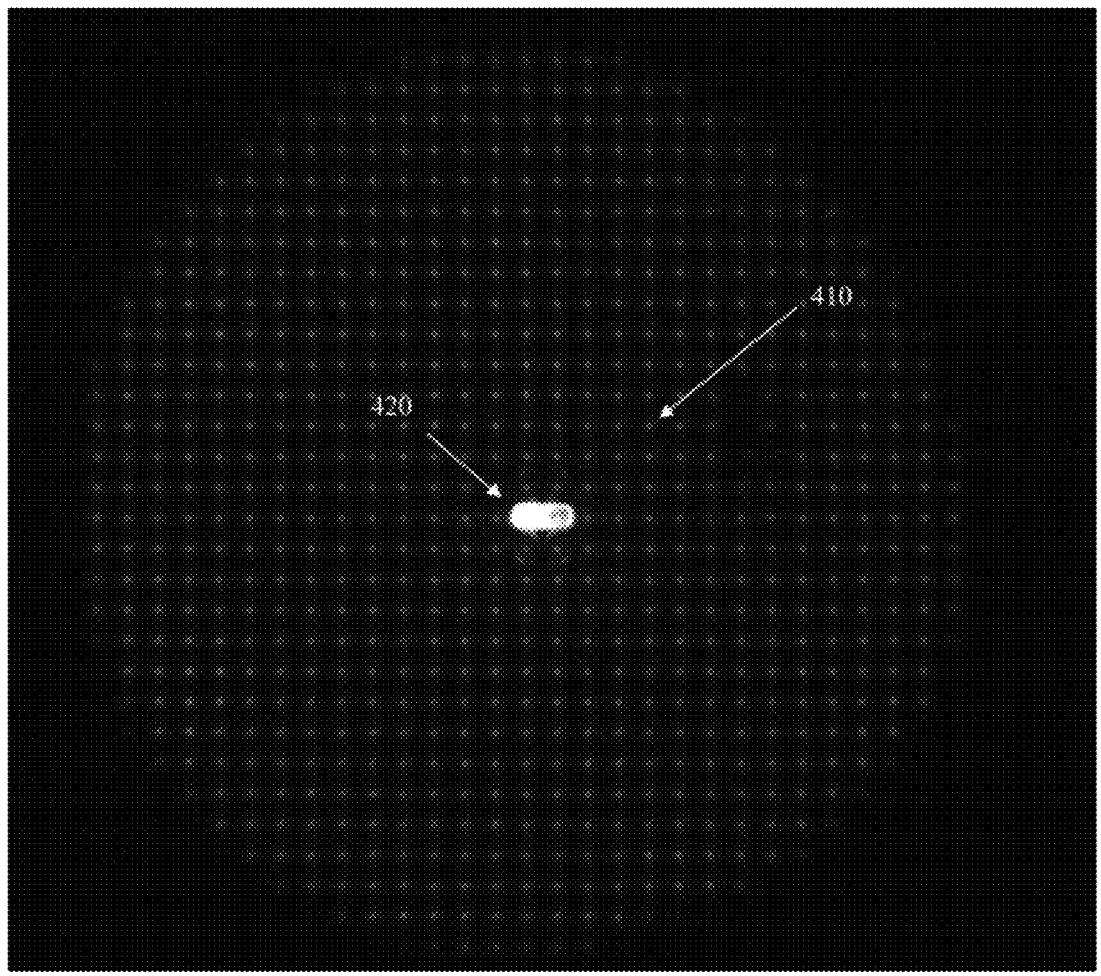
FIG. 4 illustrates an example of a raw image from a wavefront sensor produced from a model eye.

FIG. 4 illustrates an example of a raw image 400 from a wavefront sensor 16 of optical measurement instrument 10 produced from the light of return light beam 5 received from model eye 20. In particular, raw image 400 may be generated in a case where wavefront sensor 16 is a Shack-Hartmann wavefront sensor. For example, lenslet array 16a of wavefront sensor 16 may receive the return light beam 5 and in response thereto may produce image 400 on detector array 16b, including a plurality of light spots 410. Detector array 16b outputs image data corresponding to the image, including light spot data for the plurality of light spots 430, and processor 17 processes the image data to determine one or more characteristics of model eye 20.

As explained above, during the process for verifying that optical measurement instrument 10 is performing correctly, the characteristics of model eye 20 measured by are varied because of the misalignment angle θ, and this variance may be greater than an allowable tolerance for optical measurement instrument 10.

To address this problem, optical measurement instrument 10 may execute an algorithm using the single bright spot near the center of image 400, known as the corneal reflex 420, to determine whether optical instrument 10 is operating properly even when there is a significant misalignment angle θ between normal axis 29 of model eye 20 and optical axis 19 of optical measurement instrument 10. Corneal reflex 420 is produced from the reflection of the probe light beam 3 as it enters model eye 20. Corneal reflex 420 is also known in the art as the Purkinje I reflection. Other Purkinje reflections also come from the posterior cornea, anterior lens and posterior lens surfaces, and these are referred to as the Purkinje II, III and IV reflections, respectively. Purkinje analysis can be used to calculate anatomical structures of an eye such as lens curvatures and tilts.

Several embodiments will be described below.

In a first embodiment, optical measurement instrument 10 (e.g., processor 17 of optical measurement instrument 10) may execute an algorithm that uses the observed location of corneal reflex 420 to determine misalignment angle θ and to compensate the measured characteristics (e.g., sphere and/or cylinder) of model eye 20 for variances caused by the misalignment angle θ.

Corneal reflex 420 is located where the normal axis 29 to the surface of "cornea" 21 of model eye 20 is aligned with optical axis 19 of optical measurement instrument 10. When aperture 24 defined by iris 23 is located centrally around normal axis 19, and with model eye 20 aligned with optical measurement instrument 10, then corneal reflex 21 should appear in the center of the portion of image 400 corresponding to aperture 24 defined by iris 23. This can be considered to be the expected location of the corneal reflex 430.

Figure 5:
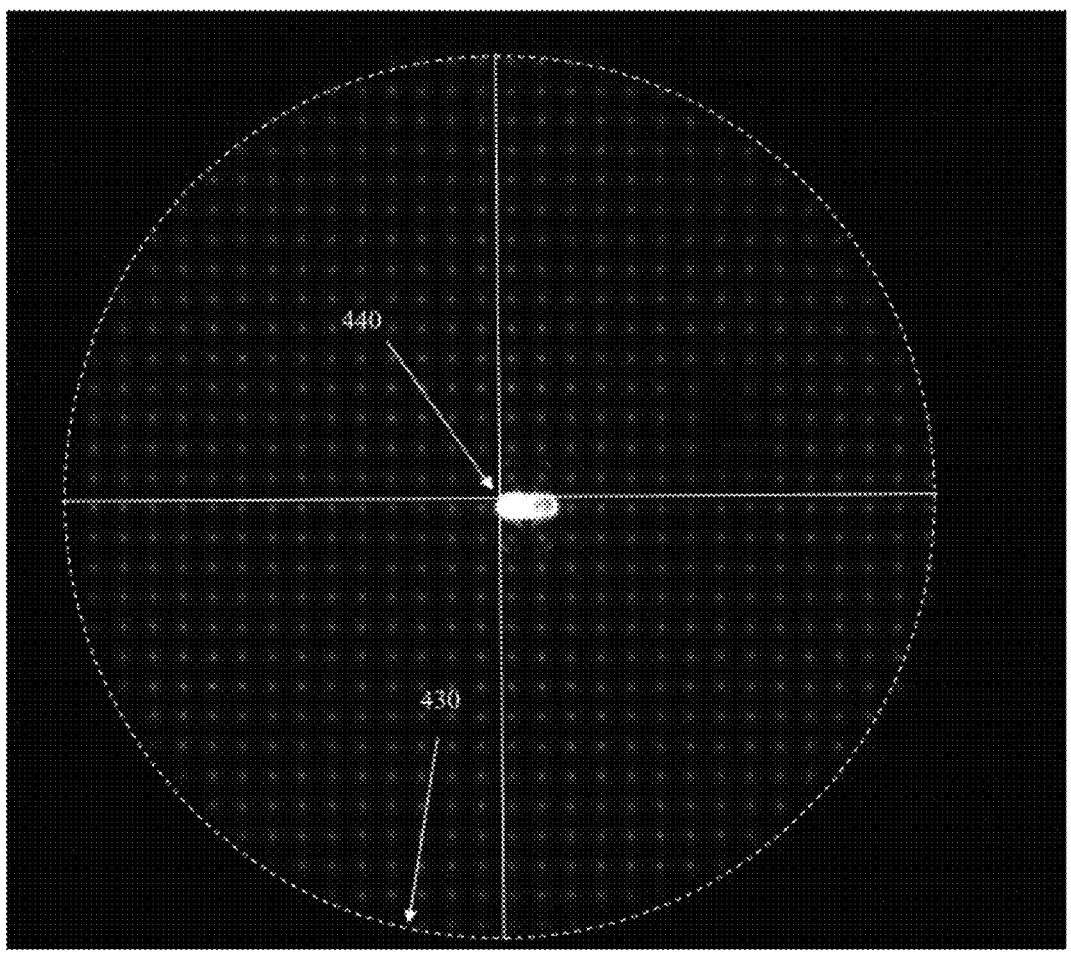
FIG. 5 illustrates an example of a raw image from a wavefront sensor and a center of a portion of the image defined by an iris of the model eye.

FIG. 5 illustrates a boundary 430, e.g. a circular boundary, circumscribing a portion of image 400 corresponding to aperture 24 defined by iris 23 of model eye 20. Processor 17 may determine boundary 430 from intensity values for the light spot data corresponding to light spots 410. Using the determined boundary 430, then optical measurement instrument 10 (e.g., processor 17 of optical measurement instrument 10) may determine an expected location 440 of the corneal reflex as the center of boundary 430.

From the observed location of corneal reflex optical measurement instrument 10 (e.g., processor 17 of optical measurement instrument 10)

Once misalignment angle θ is known, then optical measurement instrument 10 (e.g., processor 17 of optical measurement instrument 10) may compensate the measured characteristics (e.g., the sphere and cylinder values) for model eye 20 for the misalignment angle θ to produced compensated values. The compensation to be applied to the measured values can be determined from correction values stored in a memory in optical measurement instrument 10 that were previously determined from experimental measurements, or can be determined by performing a ray tracing algorithm using the misalignment angle θ. Finally, optical measurement instrument 10 (e.g., processor 17 of optical measurement instrument 10) compares the measured values to predetermined calibration values for model eye 20 to determine whether or not optical measurement instrument 10 is operating properly and within specifications. The predetermined calibration values may be determined theoretically, or experimentally during a qualification process for optical measurement instrument 10 by aligning the normal axis 29 and the optical axis 19 of optical measurement instrument 10 to within a predetermined tolerance, generating calibration image data while the normal axis 29 and the optical axis 19 are aligned within the predetermined tolerance, and processing the calibration image data to extract the calibration values.

Figure 6:
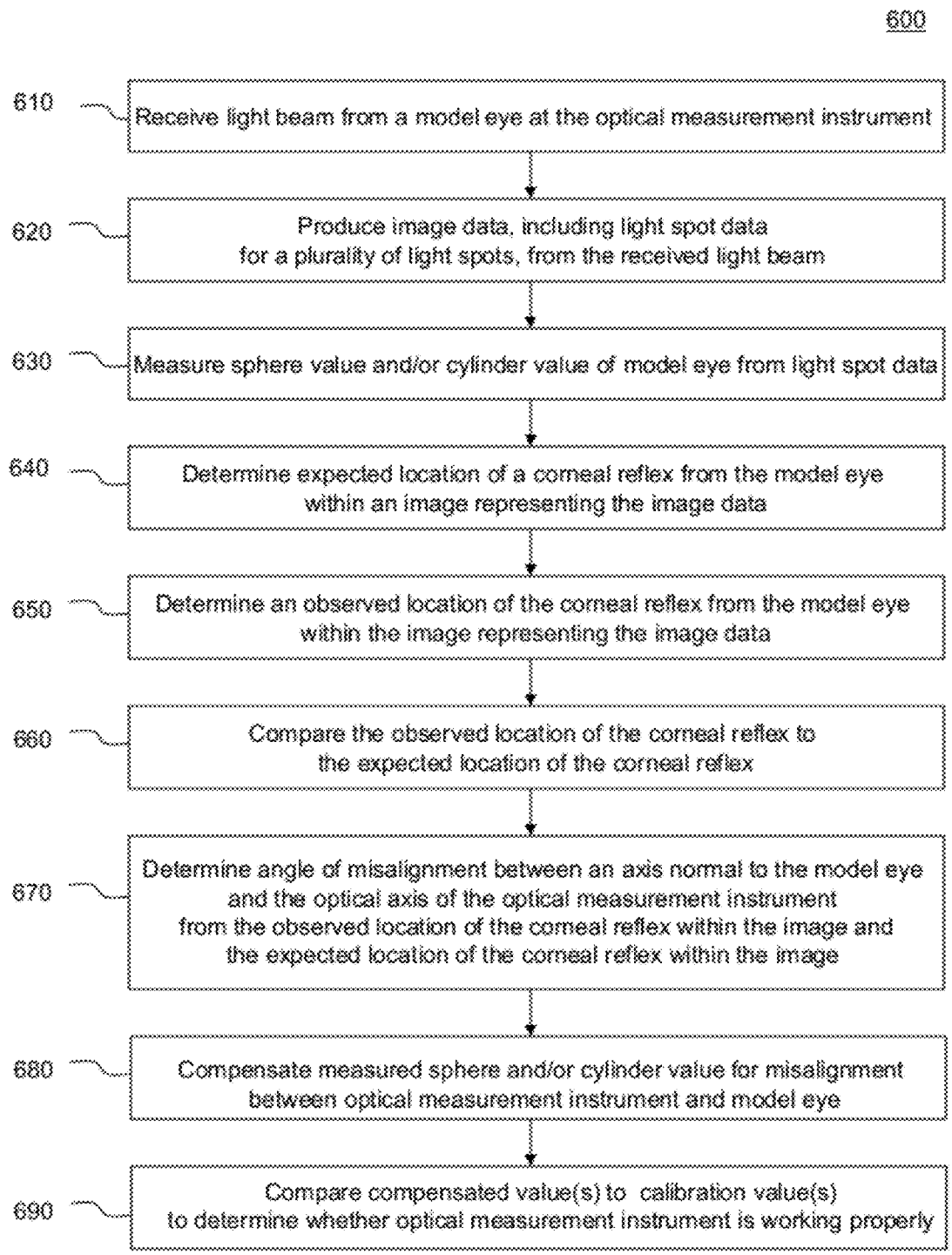
FIG. 6 shows a flowchart illustrating one embodiment of a method of verifying proper operation of an optical measurement instrument with a model eye.

FIG. 6 shows a flowchart illustrating one embodiment of a method of verifying proper operation of an optical measurement instrument with a model eye.

In a step 610, an optical measurement instrument receives a light beam from a model eye.

In a step 620, the optical measurement instrument, and particularly a wavefront sensor of the optical measurement instrument, produces image data, including light spot data for a plurality of light spots, from the received light beam.

In a step 630, the optical measurement instrument, and particularly a processor of the optical measurement instrument, calculates or measures one or more calibrated characteristics of the model eye (e.g., a sphere value and/or a cylinder value of the model eye) from the light spot data.

In a step 640, the optical measurement instrument, and particularly the processor of the optical measurement instrument, determines an expected location of a corneal reflex from the model eye within an image representing the image data.

In a step 650, the optical measurement instrument, and particularly the processor of the optical measurement instrument, determines the observed location of the corneal reflex from the model eye within the image representing the image data.

In a step 660, the optical measurement instrument, and particularly the processor of the optical measurement instrument, compares the observed location of the corneal reflex to the expected location of the corneal reflex.

In a step 670, the optical measurement instrument, and particularly the processor of the optical measurement instrument, determines an angle of misalignment between an axis normal to the model eye and the optical axis of the optical measurement instrument from the observed location of the corneal reflex within the image and the expected location of the corneal reflex within the image.

In a step 680, the optical measurement instrument, and particularly the processor of the optical measurement instrument, compensates the measured sphere value and/or measured cylinder value for the misalignment between the optical measurement instrument and the model eye.

In a step 690, the optical measurement instrument, and particularly the processor of the optical measurement instrument, compares the compensated sphere and/or cylinder value(s) to calibration value(s) that have previously been established for the model eye (e.g., in an initial qualification process for the optical measurement instrument), and which may be stored in memory associated with the processor, to determine whether the optical measurement instrument is working properly and according to its specifications.

Figure 7:
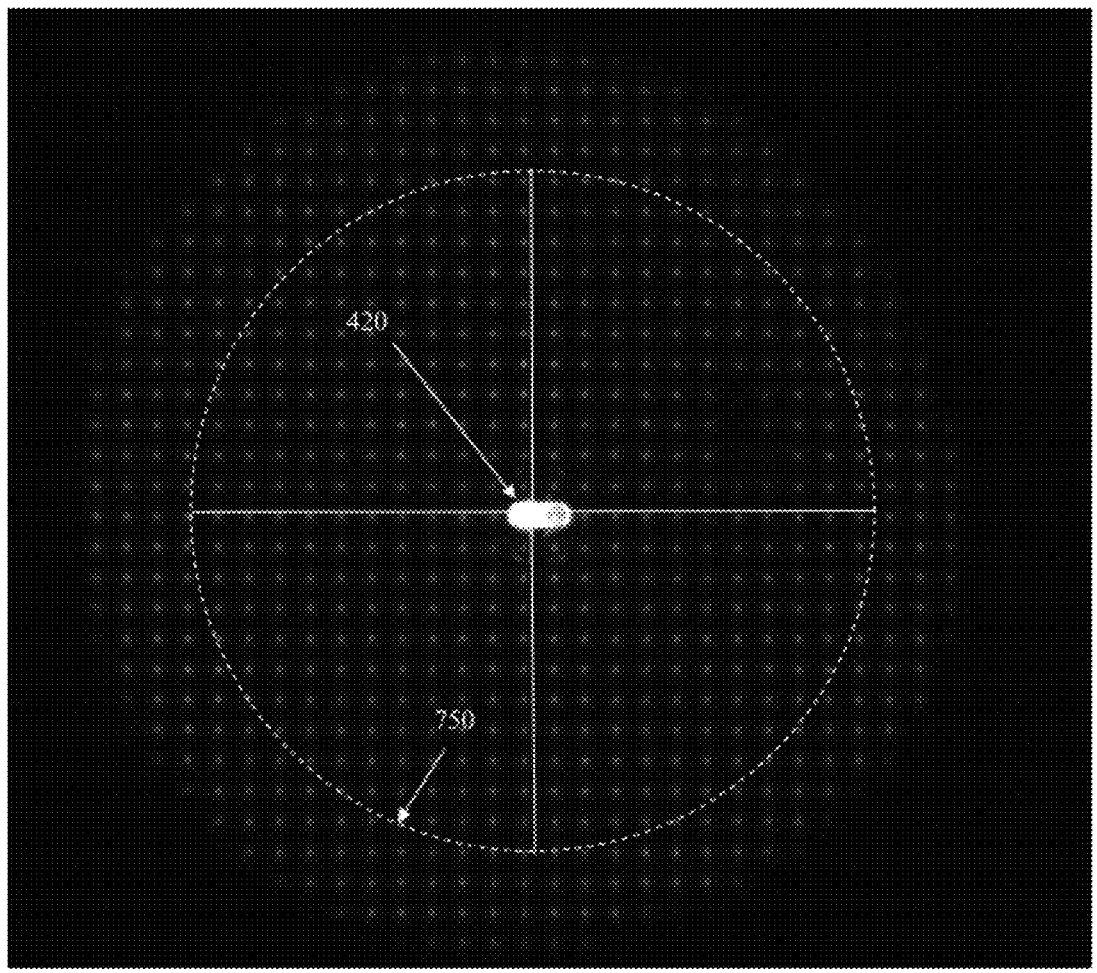
FIG. 7 illustrates an example of a raw image from a wavefront sensor and a portion of the image used for wavefront analysis.

In another embodiment, which can be described with respect to FIG. 7, processor 17 positions a wavefront analysis region 750 symmetrically around the location of corneal reflex 430, and performs its measurements of the characteristics (e.g., sphere and/or cylinder) of model eye 20 using only the portion of the image data that lies within wavefront analysis region 750. In this case, the diameter of wavefront analysis region 750 is less than the full diameter of the aperture 24 of model eye 20 defined by iris 23. For example, in an example case where aperture 24 of model eye 20 is 7 mm, then wavefront analysis region 750 may be a circular region having a diameter of 4 mm centered on the observed location of corneal reflex 430.

In yet another embodiment, optical measurement instrument 10 provides an indication via display 18 to the instrument operator of the misalignment angle θ, and the operator adjusts a mechanical mount 25 to adjust the misalignment angle θ to be within some allowed tolerance.

While preferred embodiments are disclosed herein, many variations are possible which remain within the concept and scope of the invention. Such variations would become clear to one of ordinary skill in the art after inspection of the specification, drawings and claims herein. The invention therefore is not to be restricted except within the spirit and scope of the appended claims.

I claim:

1. A method, comprising:
receiving a light beam from a model eye at an optical measurement instrument having an optical axis;
producing image data, including light spot data for a plurality of light spots, from the received light beam;
determining an observed location of a corneal reflex from the model eye within an image representing the image data; and
determining an angle of misalignment between an axis normal to a front surface of the model eye and the optical axis of the optical measurement instrument from the observed location of the corneal reflex within the image, wherein determining the angle of misalignment between the axis normal to the front surface of the model eye and the optical axis of the optical measurement instrument from the determined location of the corneal reflex within the image comprises:
establishing an expected location of the corneal reflex within the image; and
using a ray tracing algorithm to calculate the angle of misalignment between the expected location and the observed location.

2. The method of claim 1, further comprising measuring at least one of a sphere value and a cylinder value for the model eye from the light spot data.

3. The method of claim 2, further comprising compensating the at least one measured value to account for the angle of misalignment.

4. The method of claim 3, further comprising:
comparing the at least one compensated measured value to a corresponding calibration value for the optical measurement instrument; and
providing an indication that the optical measurement instrument is operating properly when a difference between the compensated measured value and the corresponding calibration value is less than a specified tolerance.

5. The method of claim 1, wherein producing the image data from the received light beam, comprises:
providing the received light beam to a Shack-Hartmann wavefront sensor; and
outputting the image data from the Shack-Hartmann wavefront sensor.

6. The method of claim 1, further comprising:
aligning the axis normal to the model eye and the optical axis of the optical measurement instrument to within a predetermined tolerance; and
generating calibration image data while the axis normal to the model eye and the optical axis of the optical measurement instrument are aligned within the predetermined tolerance; and
processing the calibration image data to extract the calibration values.

7. The method of claim 1, wherein determining an observed location of a corneal reflex from the model eye within an image represented by the image data comprises:
determining a boundary of a portion of the image corresponding to an iris of the model eye; and
determining the observed location of the corneal reflex with respect to the boundary.

8. The method of claim 1, further comprising displaying the angle of misalignment to an operator of the optical measurement instrument.

9. A measurement instrument, comprising:
one or more light sources configured to illuminate a model eye;
a light spot generator configured to receive light from the model eye and to generate a plurality of light spots from the light received from the illuminated object;
a detector configured to detect the light spots and for outputting image data, including light spot data for the plurality of light spots;
a processor configured to process the image data to determine an alignment between the measurement instrument and the model eye by:
determining an observed location of a corneal reflex from the model eye within an image representing the light spot data; and
determining an angle of misalignment between an axis normal to the model eye and an optical axis of the measurement instrument from the observed location of the corneal reflex within the image,
wherein determining the angle of misalignment between the axis normal to the front surface of the model eye and the optical axis of the measurement instrument from the determined location of the corneal reflex within the image comprises:
establishing an expected location of the corneal reflex within the image; and
using a ray tracing algorithm to calculate the angle of misalignment between the expected location and the observed location.

10. The measurement instrument of claim 9, wherein the measurement instrument is configured to measure at least one of a sphere value and a cylinder value for the model eye from the light spot data.

11. The measurement instrument of claim 10, wherein the processor is further configured to compensate the at least one measured value to account for the angle of misalignment.

12. The measurement instrument of claim 11, wherein the processor is further configured to:
compare the at least one compensated measured value to a corresponding calibration value for the measurement instrument; and
provide an indication that the measurement instrument is operating properly when a difference between the compensated measured value and the corresponding c calibration value is less than a specified tolerance.

13. The measurement instrument of claim 9, wherein the detector includes a Shack-Hartmann wavefront sensor.

14. The measurement instrument of claim 9, wherein establishing the expected location of the corneal reflex within the image comprises:

aligning the axis normal to the front surface of the model eye and the optical axis of the optical measurement instrument to within a predetermined tolerance;

generating calibration image data while the axis normal to the model eye and the optical axis of the optical measurement instrument are aligned within the predetermined tolerance; and processing the calibration image data to extract the calibration values.

15. The measurement instrument of claim 9, wherein determining the observed location of the corneal reflex from the model eye within the image represented by the image data comprises:

determining a boundary of a portion of the image corresponding to an iris of the model eye; and determining the observed location of the corneal reflex with respect to the boundary.

16. The measurement instrument of claim 9, further comprising a display, and wherein the processor is configured to display an indication of the angle of misalignment on the display.

17. A method of determining a misalignment between a measurement instrument and a model eye used to verify correct operation of the measurement instrument, by determining a difference between: (1) an observed location of a corneal reflex in an image produced by the measurement instrument from the model eye, and (2) an expected location of the corneal reflex, and using a ray tracing algorithm to calculate an amount misalignment that corresponds to a difference between the observed location and the expected location.

18. The method of claim 17, further comprising determining the expected location of the corneal reflex from a calibration image generated when the measurement instrument is aligned with the model eye.

19. The method of claim 17, further comprising determining the observed location of a corneal reflex by:

determining a boundary of a portion the image corresponding to an iris of the model eye; and determining the observed location of the corneal reflex with respect to the boundary.

20. A method, comprising:

receiving a light beam from a model eye at an optical measurement instrument having an optical axis;

producing image data, including light spot data for a plurality of light spots, from the received light beam;

determining an observed location of a corneal reflex from the model eye within an image representing the image data;

defining an analysis area within an image represented by the image data, wherein the analysis area is centered on the observed location of the corneal reflex;

measuring at least one of a sphere value and a cylinder value for the model eye from a portion of the light spot data corresponding to light spots within the analysis area; and determining an angle of misalignment between an axis normal to a front surface of the model eye and the optical axis of the optical measurement instrument from the observed location of the corneal reflex within the image, wherein determining the angle of misalignment between the axis normal to the front surface of the model eye and the optical axis of the optical measurement instrument from the determined location of the corneal reflex within the image comprises:

establishing an expected location of the corneal reflex within the image; and using a ray tracing algorithm to calculate the angle of misalignment between the expected location and the observed location.

\* \* \* \* \*